United States Patent
Toslak et al.

(10) Patent No.: US 11,154,193 B2
(45) Date of Patent: Oct. 26, 2021

(54) FUNDUS IMAGING APPARATUS WITH TRANS-PARS-PLANAR ILLUMINATION

(71) Applicant: Biolight Engineering LLC, Hinsdale, IL (US)

(72) Inventors: Devrim Toslak, Antalya (TR); Xincheng Yao, Hinsdale, IL (US)

(73) Assignee: Biolight Engineering LLC, Hinsdale, IL (US)

( * ) Notice: Subject to any disclaimer, the term of this patent is extended or adjusted under 35 U.S.C. 154(b) by 660 days.

(21) Appl. No.: 16/116,234

(22) Filed: Aug. 29, 2018

(65) Prior Publication Data

US 2019/0008382 A1    Jan. 10, 2019

Related U.S. Application Data

(63) Continuation of application No. PCT/US2017/020449, filed on Mar. 2, 2017.

(60) Provisional application No. 62/303,357, filed on Mar. 3, 2016.

(51) Int. Cl.
| A61B 3/12 | (2006.01) |
| A61B 3/00 | (2006.01) |
| A61B 3/14 | (2006.01) |
| A61B 5/00 | (2006.01) |

(52) U.S. Cl.
CPC .............. *A61B 3/12* (2013.01); *A61B 3/0008* (2013.01); *A61B 3/14* (2013.01); *A61B 5/6898* (2013.01)

(58) Field of Classification Search
CPC ....... A61B 3/12; A61B 5/6898; A61B 3/0008; A61B 3/14

USPC ........................................................ 351/208
See application file for complete search history.

(56) References Cited

U.S. PATENT DOCUMENTS

| 3,954,329 | A  | 5/1976  | Pomerantzeff |
| 4,061,423 | A  | 12/1977 | Pomerantzeff |
| 6,267,752 | B1 | 7/2001  | Svetliza |
| 7,712,901 | B2 | 5/2010  | Wernick et al. |
| 8,836,778 | B2 | 9/2014  | Ignatovich et al. |

(Continued)

OTHER PUBLICATIONS

Pomerantzeff, O., Webb, R. H. & Delori, F. C. Image formation in fundus cameras. Investigative ophthalmology & visual science 18, 630-637 (1979).

(Continued)

*Primary Examiner* — Mohammed A Hasan
(74) *Attorney, Agent, or Firm* — Crowell & Moring LLP

(57) ABSTRACT

Methods and apparatus are described for illuminating the fundus of an eye for wide-angle fundus photography. The present disclosure delivers light through a pars planar area of the eye for illuminating the interior of the eye, or through an eyelid and a pars plana of the eye. Trans-pars-planar illumination frees the entire pupil for imaging and therefore eliminates need for pupil dilation or complex balancing between illumination and imaging in previous wide-angle fundus photography based on trans-pupillary illumination. Additionally, the present disclosure discloses, when an optical fiber bundle multiple-channel trans-pars-planar illuminator placed adjacent to the pars plana, at least one optical fiber in the optical fiber bundle aligns with the pars plana to deliver light through the pars plana into the fundus of the eye, thus eliminating the previous problem of having to move an optical fiber to search a location of the pars plana.

17 Claims, 12 Drawing Sheets

(56) References Cited

U.S. PATENT DOCUMENTS

| | | |
|---|---|---|
| 8,967,806 B2 | 3/2015 | Bublitz et al. |
| 9,060,718 B2 | 6/2015 | Lawson et al. |
| 9,179,840 B2 | 11/2015 | Su |
| 2007/0030448 A1 | 2/2007 | Biernet et al. |
| 2007/0159600 A1* | 7/2007 | Gil ................ A61B 3/0008 351/221 |
| 2013/0222763 A1 | 8/2013 | Bublitz et al. |
| 2015/0005750 A1 | 1/2015 | Kelleher et al. |
| 2015/0055094 A1* | 2/2015 | Boate ................ A61B 3/14 351/206 |

OTHER PUBLICATIONS

D. Toslak, D. Thapa, Y. Chen, M. K. Erol, R. V. Paul Chan, and X. Yao, "Trans-palpebral illumination: an approach for wide-angle fundus photography without the need for pupil dilation," Opt Lett 41, 2688-2691 (2016).

B. Wang, D. Toslak, M. N. Alam, R. V. P. Chan, and X. Yao, "Contact-free trans-pars-planar illumination enables snapshot fundus camera for nonmydriatic wide field photography," Sci Rep 8, 8768 (2018).

International Search Report and Written Opinion of the International Searching Authority regarding International Appl. No. PCT/US2017/020449, 11 pages, dated May 11, 2017.

Search Report with translation and Office Action regarding Chinese Appl. No. 201780024393.1, dated May 18, 2020, 11 pages.

\* cited by examiner

Delivering light emitted from a light source into an input end of an optical fiber bundle comprising at least a first optical fiber and a second optical fiber, wherein the light comprises a first light and a second light
1402

Figure 14A

Sequentially delivering, by a light switch device, the first light into the first end of the first optical fiber and the second light into the first end of the second optical fiber
1404

Figure 14B

When the imaging light is from the first light from the first optical fiber, forming, by the imaging lens, a first optical image from the imaging light; and
when the imaging light is from the second light from the second optical fiber, forming, by the imaging lens, a second optical image from the imaging light
1406

Figure 14C

FUNDUS IMAGING APPARATUS WITH TRANS-PARS-PLANAR ILLUMINATION

RELATED APPLICATIONS

This application claims priority to PCT Patent Application No. PCT/US2017/020449, filed on Mar. 2, 2017, which claims priority to U.S. Provisional Patent Application No. 62/303,357, filed Mar. 3, 2016, and entitled "METHODS AND DEVICES FOR FUNDUS PHOTOGRAPHY EMPLOYING TRANS-PALPEBRAL AND TRANS-SCLERAL ILLUMINATION," both of which are incorporated by reference in their entireties.

TECHNICAL FIELD

This disclosure relates to fundus camera and retinal imaging, and in more specifically, to a fundus imaging apparatus with trans-pars-planar illumination for performing non-mydriatic and wide-angle fundus photography.

BACKGROUND

Wide-angle fundus photography is useful for screening, diagnosis and treatment evaluation of eye disease, such as retinopathy of prematurity (ROP), diabetic retinopathy (DR), choroidal masses and choroidal metastases, choroidal dystrophies, etc. One prior solution of fundus photography illuminates an interior of the eye through a pupil of the eye, also referred to herein as trans-pupillary illumination. The trans-pupillary illumination has some drawbacks. For example, because a portion of the pupil is used for illumination, only a remaining portion of the pupil may be used for imaging, thus limiting the field of view for imaging. The trans-pupillary illumination method may be best used for performing small angle fundus photography. For obtaining wide-angle fundus photography, pupil dilation may be required to increase the pupil size accessible for imaging. The pharmacological treatment required for pupil dilation in mydriatic fundus imaging may produce serious side effects, particularly for newborns in which the neural system is still not mature. Therefore, a non-mydriatic fundus imaging apparatus for wide-angle retinal examination is desirable to improve the management of eye diseases. This disclosure is to provide a fundus imaging apparatus with trans-pars-planar illumination for performing non-mydriatic and wide-angle fundus photography.

BRIEF DESCRIPTION OF THE DRAWINGS

The system and method described below may be better understood with reference to the following drawings and description of non-limiting and non-exhaustive embodiments. The components in the drawings are not necessarily to scale. Emphasis instead is placed upon illustrating the principles of the disclosure.

FIG. 14A shows a block diagram of an alternative implementation of the step 1302 in FIG. 13;

FIG. 14B shows a block diagram of an alternative implementation of the step 1304 in FIG. 13;

FIG. 14C shows a block diagram of an alternative implementation of the step 1314 in FIG. 13.

DETAILED DESCRIPTION

Figure 1:
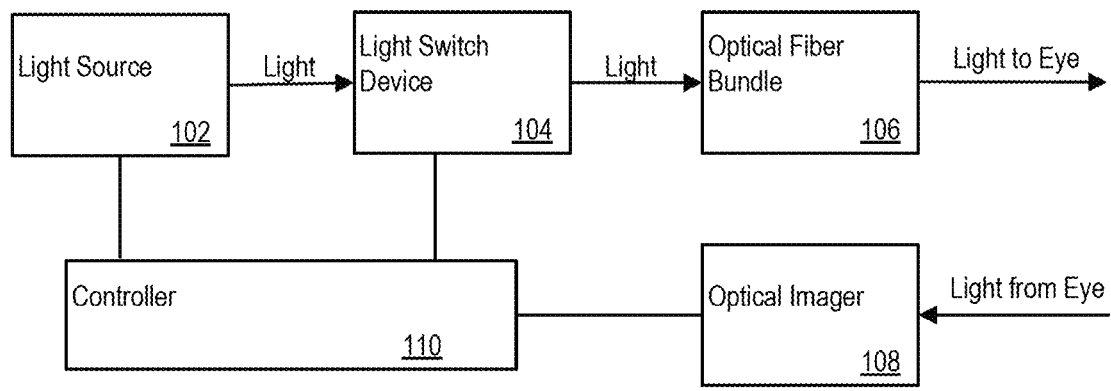
FIG. 1 shows an example architecture for a fundus imaging apparatus for performing wide-angle fundus photography with trans-pars-planar illumination.

The present disclosure describes methods and apparatus for trans-pars-planar illumination to illuminate the fundus of an eye to perform non-mydriatic and wide-angle fundus photography. Rather than delivering light through a pupil of the eye to illuminate the fundus of the eye, the present disclosure delivers light to illuminate the fundus of the eye through a pars planar area of the eye, also referred to herein as trans-pars-planar illumination, in which the light can be delivered through the sclera or through an eyelid of the eye, also referred to herein as trans-palpebral illumination. Such illumination frees an entire area of the pupil for imaging and therefore eliminates the need for pupil dilation as well as complex balancing between illumination and imaging in previous wide-angle fundus photography based on trans-pupillary illumination. Trans-palpebral illumination through the eyelid may also avoid having a direct contact of the apparatus with the sclera of the eye, thus may be safer and less uncomfortable to the eye. Additionally, the present disclosure discloses an optical fiber bundle multiple channel trans-pars-planar illuminator to deliver light into the eye, and when an output end of the optical fiber bundle is placed on either a sclera or an eyelid around the pars plana, at least one optical fiber in the optical fiber bundle can deliver light through the pars plana of the eye, thus eliminating the previous problem of having to move an output end of an optical fiber to search for the location of the pars plana of the eye.

In one aspect for an apparatus of performing fundus photography, the apparatus includes an optical fiber bundle multiple channel trans-pars-planar illuminator having one or more optical fibers. The input end of the optical fiber bundle is configured to receive light emitted from a light source. The output end of the optical fiber bundle is configured to deliver illuminating light through an eyelid and a pars planar area into the fundus of an eye for illumination. The apparatus further include an optical imager configured to output image data based on imaging light from the interior fundus of the eye detected through a pupil of the eye. The imaging light may include a portion of the illuminating light scattered or reflected by the fundus of the eye.

In another aspect for a fundus imaging apparatus with trans-pars-planar illumination for performing fundus photography, the apparatus includes an optical fiber bundle, i.e., multiple-channel trans-pars-planar illuminator, having a first optical fiber and a second optical fiber. The output end of the optical fiber bundle is configured to deliver illuminating light through a pars planar area into the fundus of an eye for illumination. The fundus imaging apparatus further includes a light switch device for receiving light emitted from a light source and sequentially delivering the light into a first end of the first optical fiber and a first end of the second optical fiber. A fundus imaging apparatus may be configured to sequentially output image data based on imaging light from the fundus of the eye detected through the pupil of the eye. The imaging light may include a portion of the illuminating light scattered or reflected by the interior fundus of the eye. The fundus imaging apparatus further includes a controller configured to communicate with the light switch device and obtain the image data from the optical imager.

In another aspect of an illumination method of illuminating the fundus of an eye through an eyelid of the eye, the illumination method includes delivering light emitted from a light source into an input end of an optical fiber bundle trans-pars-planar illuminator comprising one or more optical fibers. The illumination method further includes transmitting, by the optical fiber bundle, the light from the input end of the optical fiber bundle to an output end of the optical fiber bundle. The illumination method further includes delivering, by the output end of the optical fiber bundle, a portion of the light through the eyelid and a pars planar area of the eye into the interior of the eye, wherein the illuminating light comprises a portion of the light, and illuminating, by the illuminating light, the fundus of the eye.

In another aspect of an illumination method of illuminating the fundus of an eye through a pars planar area of the eye, the illumination method includes delivering light emitted from a light source into an input end of an optical fiber bundle trans-pars-planar illuminator comprising at least a first optical fiber and a second optical fiber. The illumination method further includes transmitting, by the optical fiber bundle, the light from the input end of the optical fiber bundle to an output end of the optical fiber bundle. The illumination method further includes delivering, by the output end of the optical fiber bundle, a portion of the light through a pars planar area of the eye into the fundus of the eye, and illuminating, by the portion of the light, the fundus of the eye.

In another aspect of a method of performing fundus photography of an eye, the method includes either one of the two illumination methods as described above. The method further includes collecting imaging light with a collecting lens through a pupil of the eye. The imaging light may include a portion of the illuminating light scattered or reflected by the fundus of the eye. The method further includes forming, by an imaging system, an optical image from the imaging light.

Subject matter will now be described more fully hereinafter with reference to the accompanying drawings, which form a part hereof, and which show, by way of illustration, specific example embodiments. Subject matter may, however, be embodied in a variety of different forms and, therefore, covered or claimed subject matter is intended to be construed as not being limited to any example embodiments set forth herein. A reasonable board scope for claimed or covered subject matter is intended. Among other things, for example, subject matter may be embodied as methods, devices, components, or systems. Accordingly, embodiments may, for example, take the form of hardware, software, firmware or any combination thereof.

Throughout the specification and claims, terms may have nuanced meanings suggested or implied in context beyond an explicitly stated meaning. Likewise, the phrase "in one embodiment" as used herein does not necessarily refer to the same embodiment and the phrase "in another embodiment" as used herein does not necessarily refer to a different embodiment. It is intended, for example, that claimed subject matter include combinations of example embodiments in whole or in part.

In general, terminology may be understood at least in part from usage in context. For example, terms, such as "and", "or", or "and/or," as used herein may include a variety of meanings that may depend at least in part upon the context in which such terms are used. Typically, "or" if used to associate a list, such as A, B or C, is intended to mean A, B, and C, here used in the inclusive sense, as well as A, B or C, here used in the exclusive sense. In addition, the term "one or more" or "at least one" as used herein, depending at least in part upon context, may be used to describe any feature, structure, or characteristic in a singular sense or may be used to describe combinations of features, structures or characteristics in a plural sense. Similarly, terms, such as "a", "an", or "the", again, may be understood to convey a singular usage or to convey a plural usage, depending at least in part upon context. In addition, the term "based on" or "determined by" may be understood as not necessarily intended to convey an exclusive set of factors and may, instead, allow for existence of additional factors not necessarily expressly described, again, depending at least in part on context.

FIG. 1 shows an apparatus including a light source 102, a light switch device 104, an optical fiber bundle trans-pars-planar illuminator 106, an optical imager 108, and a controller 110. The controller 110 is in communication with the light source 102, the light switch device 104, and the optical imager 108. The light source 102 emits light. The light switch device 104 switches the light from the light source into one or more optical fibers in the optical fiber bundle 106 either sequentially or simultaneously. The optical fiber bundle 106 delivers the light from the light switch device 104 to an eye. The optical imager receives light from the eye and outputs image data.

The light source 102 may comprise one or more light sources capable of emitting visible or invisible light. The one or more light sources may emit light either sequentially or simultaneously. The light emitted from the one or more light sources may have a same light intensity or different intensities. The time, duration, and intensity of each of the one or more light sources in the light source 102 may be controlled by a pre-programmed instructions stored in the light source 102 or may be controlled by the instructions from the controller 110 via communication with the controller 110.

The type of each of the one or more light sources may include, but is not limited to, an electric discharge light source, for example, an arc lamp or a high-intensity discharge lamp; an incandescence light source, for example, a halogen lamp or an incandescent light lamp; a laser, for example a continuous-wave laser or a pulsed laser; or a light-emitting diode (LED).

Figure 2:
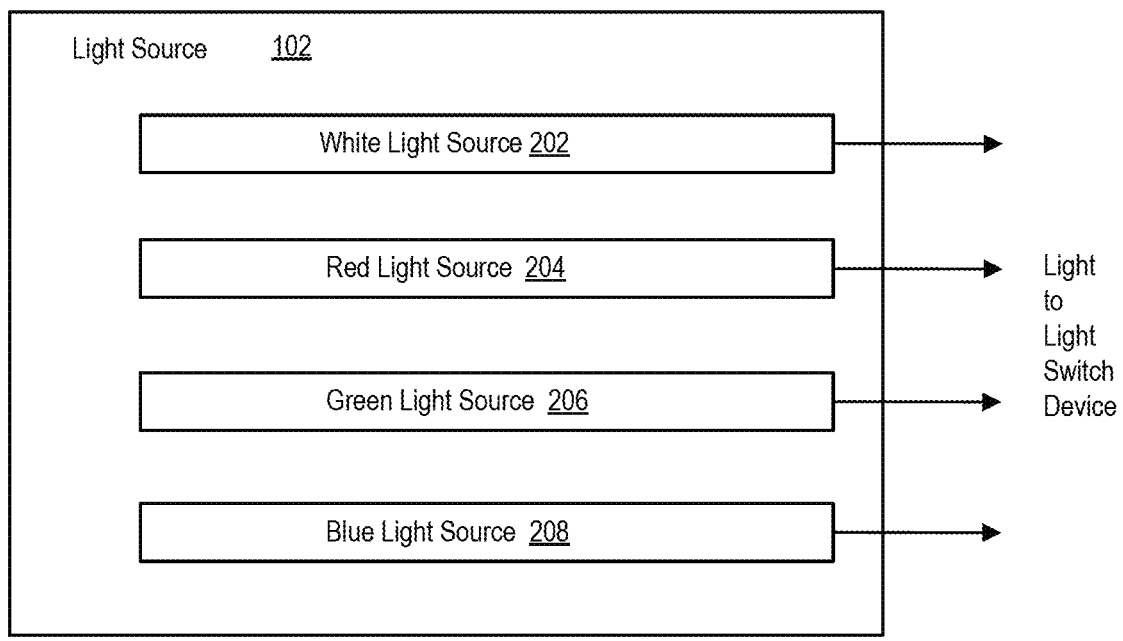
FIG. 2 shows an exemplary diagram of the light source in FIG. 1.

The light source 102 may comprise a single light source or a plurality of light sources, and each light source may emit white light, one or more single color light, or a combination of white and one or more color light. FIG. 2 shows an exemplary light source emitting light to the light switch device. The light source in FIG. 2 comprises a combination of a white light source 202, a red light source 204, a green light source 206, and a blue light source 208, which may emit light either sequentially or simultaneously with same or different light intensities. For example, the red light source 204, the green light source 206, and the blue light source 208 may sequentially emit red light, green light, and blue light respectively. Alternatively, the red light source 204, the green light source 206, and the blue light source 208 may emit light simultaneously.

In another embodiment, the light source 102 may comprises one or more light sources. Each of the one or more light sources may emit visible light, near infra-red light, infra-red light, ultra-violet light, or a combination of the light herein. The one or more light sources may emit light either sequentially or simultaneously with same or different light intensities.

Types of light sources may be selected based on availability, cost and the imaging structures in the interior of the eye for fundus photography. For example, visible light source may be chosen to image retinal structures and blood vessels in the interior of the eye, and near infrared light source may be chosen to image choroid blood vessels.

The light switch device 104 receives light from the light source 102 and may comprise one or more light switch modules capable of delivering the light into at least one optical fiber of the optical fiber bundle illuminator 106. The light switch device 104 is in communication with the controller 110, and is controlled by the instructions via communication with the controller 110 to switch light emitted from the light source into at least one optical fiber of the optical fiber bundle 106. When the light source 102 comprises one or more light sources emitting light simultaneously, the light switch device 104 may comprise one or more light switch modules, so that each of the one or more light sources has a corresponding light switch module in the light switch device. Each light switch module is capable of simultaneously delivering the light emitted from the corresponding light source into at least one optical fiber of the optical fiber bundle illuminator 106.

The type of each of the one or more light switch modules may include, but is not limited to, a stepper motor optical switch, a prism optical switch, or a microelectromechanical system (MEMS) optical switch.

The optical bundle 106 receives light from the optical switch device 104 and delivers light to the fundus of an eye. The optical fiber bundle illuminator 106 may contain one or more optical fibers. The light may be sequentially transmitted through the one or more optical fibers or a subset of the one or more optical fibers. Alternatively, the optical bundle illuminator 106 may comprise one or more optical fiber subsets, and each optical fiber subset may comprise one or more optical fibers. The light may be sequentially transmitted through the one or more optical fiber subsets for localizing the pars plana and fundus imaging.

Figure 3:
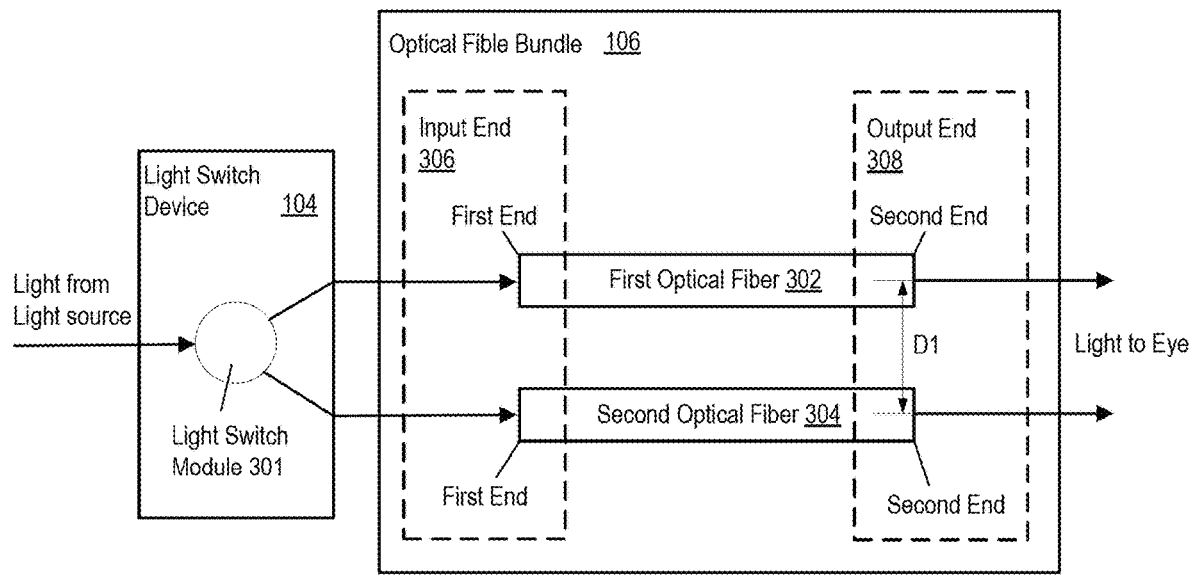
FIG. 3 shows an exemplary diagram of the optical fiber bundle illuminator and the optical switch device in FIG. 1.

FIG. 3 shows one exemplary embodiment of the light switch device 104 and the optical fiber bundle illuminator 106. The light switch device 104 comprises a light switch module. The optical fiber bundle illuminator 106 comprises a first optical fiber 302 and a second optical fiber 304. The light switch device 104 is in communication with the controller 110 and receives instructions from the controller 110 to switch light emitted from the light source into a first end of the first optical fiber and a first end of the second optical fiber either simultaneously or sequentially. The first end of the first optical fiber and the first end of the second optical fiber form an input end 306 of the optical fiber bundle illuminator. The first optical fiber 302 transmits light from the first end of the first optical fiber to a second end of the first optical fiber. The second optical fiber 304 transmits light from the first end of the second optical fiber to a second end of the second optical fiber. The second end of the first optical fiber and the second end of the second optical fiber form an output end 308 of the optical fiber bundle, delivering the light towards the fundus of an eye. The light from the second ends of the first optical fiber and the second optical fiber may be delivered either simultaneously or sequentially towards the fundus of the eye. Although FIG. 3 shows two optical fibers in the optical fiber bundle illuminator 106, the optical fiber bundle illuminator may comprise any number of optical fibers in other implementations.

Figure 4:
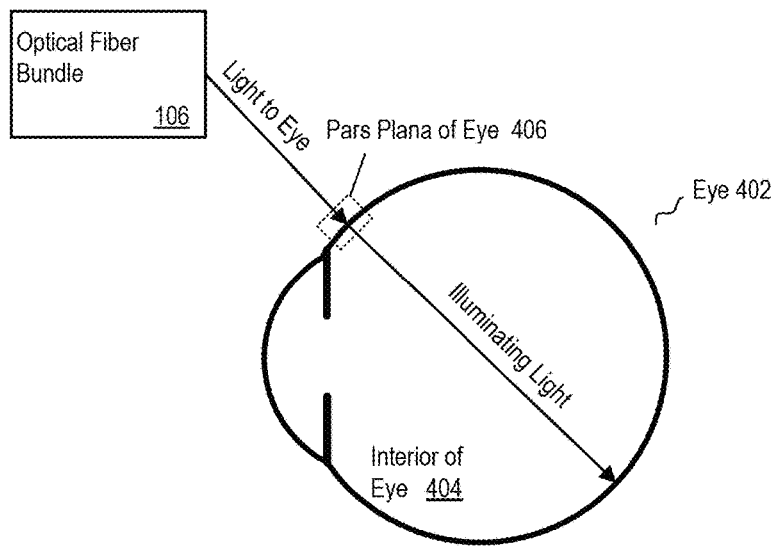
FIG. 4 shows an exemplary implementation of trans-pars-planar illumination, i.e., delivering, by an optical fiber bundle, light through the pars plana of an eye into an interior fundus of the eye.

As shown in FIG. 4, the optical fiber bundle illuminator 106 may be placed adjacent to a pars planar area of an eye, so that at least one optical fiber of the optical fiber bundle may be aligned with the pars plana of the eye 406 to permit light to be delivered through the pars plana into the interior of the eye 404 for illumination. In order to achieve high light delivering efficiency, the output end of the optical fiber bundle illuminator may be disposed close to the pars plana of the eye 406, and the light delivered from the optical fiber bundle illuminator 106 may be close to perpendicularly incident on an outer surface of the pars plana of the eye. In one exemplary embodiment, the output end of the optical fiber may make direct contact with the sclera of the eye, so that the optical fiber bundle illuminator 106 may deliver a portion of the light directly through the pars plana of the eye. In another exemplary embodiment, the output end of the optical fiber may make direct contact with an outside surface of the eyelid, so that the optical fiber bundle illuminator may first deliver the light through the eyelid and then deliver a portion of the light through the pars plana of the eye 406. Disposing the output end of the optical fiber bundle illuminator on the eyelid, rather than on the sclera, avoids making direct contact with the pars plana 406 or the sclera of the eye, thus may be safer and less uncomfortable to the eye. Depending on the incident angle or incident location of the light delivered on the eye from the second ends of the first and second optical fibers, a portion of the light may transmit through the pars plana or its surrounding area on the sclera into the interior fundus of the eye for illumination. Illuminating light comprises the portion of the light transmitting into the interior fundus of the eye for illumination. Furthermore, the light delivered from the optical fiber bundle illuminator 106 is not limited to be perpendicularly incident on the outer surface of the pars plana, and may be any angle permitting the light transmitting through the pars plana.

Furthermore, as shown in FIG. 3, the second ends of the first optical fiber 302 and the second optical fiber 304 may be spaced apart by a pre-defined distance D1 along an anterior-posterior direction of the eye. The pre-defined distance D1 may be a fixed length, such as 1 mm, 2.5 mm, or a length between 0 and 10 mm. Alternatively, the pre-defined distant D1 may be determined by a size of the pars plana of the eye, such as a third of the size of the pars plana or a ratio of the size of the pars plana between 0.0001 and 1. Thus, light from the second ends of the first optical fiber 302 and the second optical fiber 304 may be delivered at different locations on the eye, also referred to herein as light delivery locations relative to the center of the pars plana. The light delivery locations may be at the pars plana, an anterior of the pars plana, or a posterior of the pars plana. Therefore, when the light switch device sequentially delivers light into the first and second optical fibers, the light delivery locations corresponding to the second ends of the first and second optical fibers sequentially change. Because a quality of the illumination of the interior fundus of the eye is sensitive to the light delivery location relative to the center of the pars plana, the quality of the illumination may change when the light delivery location changes. Thus, the present disclosure provides a fast and convenient method to change the quality of the illumination of the interior fundus of the eye without having to move the output end of the optical fiber bundle illuminator. A selection of high quality illumination may be based on a visual quality or a quantitative image feature analysis of image data corresponding to illumination at different light delivery locations. The quantitative image feature analysis may include a property of image data, such as an intensity, a contrast or a spectral property.

The advantages of using an light switch device 104 to sequentially deliver light into the one or more optical fibers in the optical fiber bundle illuminator 106 (hereinafter "light switching") over moving the output end of the optical fiber bundle illuminator (hereinafter "moving fiber") may have several aspects. For example, light switching between a fixed array of optical fibers may be much faster than moving fiber; light switching may have better accuracy and precision than moving fiber; and light switching may be less uncomfortable to the eye than moving the optical fiber adjacent to the eye. An apparatus with light switching between a fixed array of optical fibers may be easier and more convenient for users to operate than an apparatus that must be repositioned by moving the optical fiber. An apparatus with light switching may also be less costly than an apparatus with moving fiber.

Figure 5:
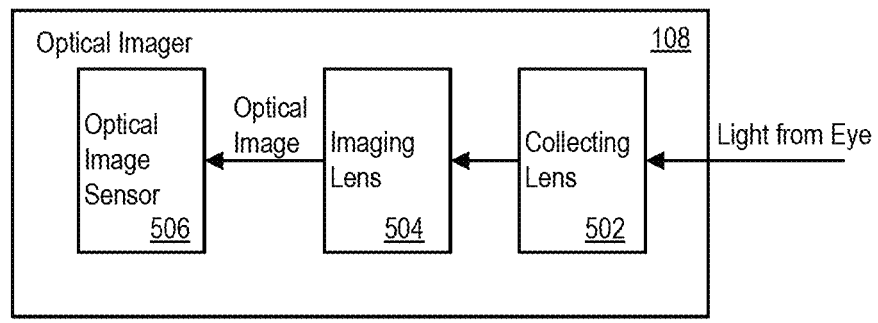
FIG. 5 shows an exemplary diagram of the fundus imaging apparatus in FIG. 1.

The optical imager 108 receives light from the eye and outputs image data. The optical imager 108 may include one or more optical components to collect the light from the eye and form an optical image. The optical image may be displayed for direct observation by users. Alternatively, the optical imager 108 may further include one or more optical image sensors to transform the optical image to image data and output the image data. FIG. 5 shows one exemplary embodiment of an optical imager 108, which comprises a collecting lens 502, an imaging lens 504, and an optical image sensor 506.

The collecting lens 502 may be an ocular lens and placed close to and in front of a cornea of an eye, so that the collecting lens may collect as much light as possible through a pupil of the eye transmitting from an interior of the eye. Because the whole pupil of the eye may be used by the collecting lens to collect light, wide-angle fundus photography may be achieved. The imaging lens 504 may comprises one or more lenses to form the optical image. The optical image sensor 506 may transform the optical image into image data. The optical image sensor 506 may output the image data. The optical image sensor 506 may further perform image processing on the image data. The image processing may include, but is not limited to, image intensity adjustment, spectral color adjustment, image contrast adjustment, image cropping, or image overlay. Alternatively, a device may obtain the image data from the optical image sensor and perform image processing on the obtained image data. The optical imager is not limited to the disclosure in FIG. 5. The optical imager may further comprise other optical component, for example, a mirror, a prism, and a beam splitter.

Figure 6A:
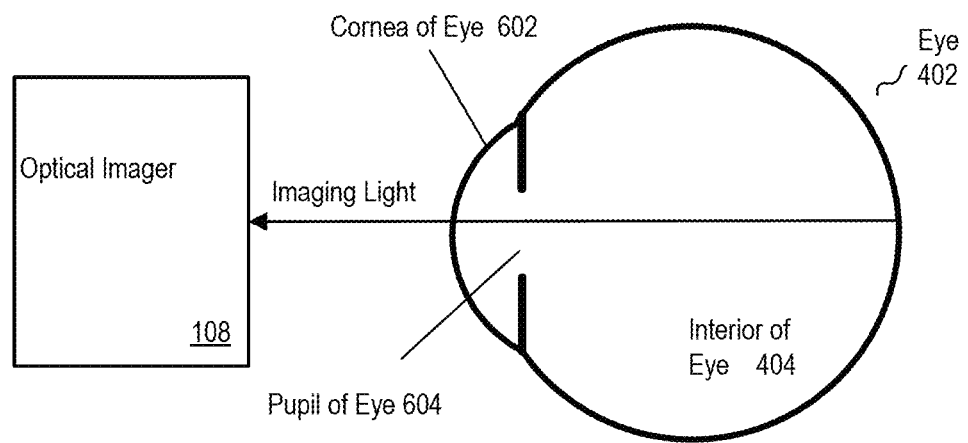
FIG. 6A shows an exemplary implementation of an fundus imaging apparatus for collecting imaging light through a pupil of the eye from the interior fundus of the eye.

FIG. 6A shows one exemplary embodiment of an optical imager 108 disposed in front of a cornea of the eye 602 to receive imaging light transmitting from the interior of the eye 404 through a pupil of the eye 604. Because the whole pupil of the eye may be used by the optical imager 108 to collect imaging light, wide-angle fundus photography may be achieved without the need of pharmacologically pupil dilation.

An optical image sensor 506 in an optical imager 108 may be a camera sensor of a handheld electronic device. The handheld electronic device may include, but is not limited to, a tablet, a smartphone, or similar electronic device with a camera. A camera lens of the camera on the handheld electronic device may be part of the imaging lens and form an optical image on the camera sensor. The camera sensor may transform the optical image into image data. The image data may be displayed on a display of the handheld electronic device. Alternatively, the image data may be output to other device or to a network via wired or wireless communication.

Figure 6B:
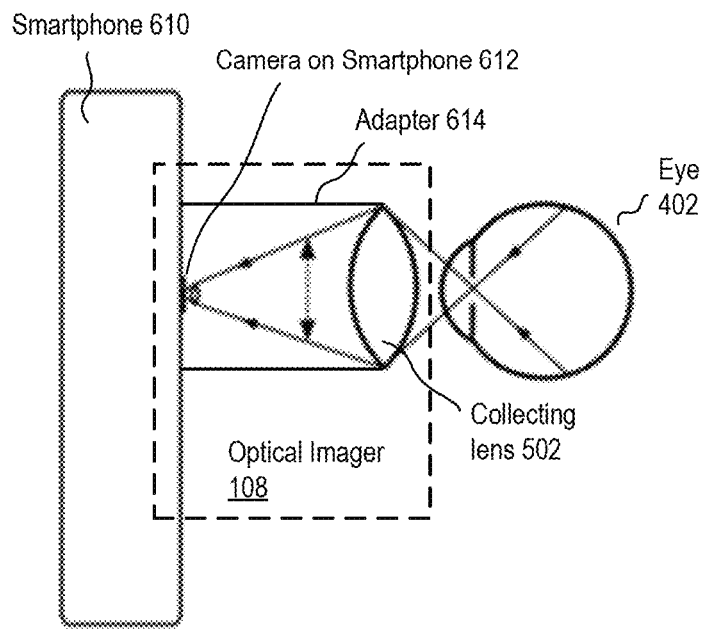
FIG. 6B shows an exemplary implementation of using a camera on a smartphone to form an fundus image and transform the fundus image to image data.

FIG. 6B shows one exemplary embodiment of using a camera 612 on a smartphone 610 to form an optical image 108 and transform the optical image to image data. To increase efficiency of collecting imaging light from the interior of the eye through a pupil of an eye, a collecting lens 502 may be disposed close to a cornea of the eye and between a camera lens of the smartphone and the cornea of the eye by an adapter 614 attached to the smartphone 610. The collecting lens 502 may be larger than the camera lens of the smartphone so that the collecting lens 502 may collect the imaging light through the pupil of the eye 604 from the interior of the eye 404 at a wide-angle. The camera lens of the smartphone may form the optical imager corresponding to the collected imaging light, and a camera sensor of the smartphone may transform the optical image into image data. The smartphone 610 may further display the image data as an image on a display of the smartphone, output the image data through input-output ports or wireless communication, or save the image data as an image file to internal memory or removable memory device. The smartphone 610 may further be configured to perform imaging processes on the image data, for example, select a particular image with a higher image quality among a group of images or overlay several images together to obtain an overlay image.

Furthermore, the output end of the optical fiber bundle illuminator 308 comprises one or more second ends of optical fibers in the optical fiber bundle illuminator, and may be arranged in a pre-defined pattern. The one or more second ends of the optical fibers may form a planar interface so that the one or more second ends are at the same plane. Alternatively, the one or more second ends of the optical fibers may form a curved interface, whose curvature may be similar to a curvature of a sclera of an eye around a pars plana of the eye, so that, when the output end of the optical fiber bundle illuminator is disposed on either the sclera or an eyelid of the eye, each of the one or more second ends of the optical fibers may be close to a surface of the eye.

The pre-defined pattern of the one or more second ends of the optical fibers may be an array pattern, which comprises one or more rows and each row may comprise one or more columns. One or more second ends of the optical fibers in each row or each column may be arranged along a straight line. Alternatively, one or more second ends of the optical fibers in each row or each column may be arranged along a curve line. In one embodiment, one or more second ends of the optical fibers in one or more rows may be arranged as an arc shape, whose curvature is similar to the curvature of the pars plana of the eye, so that the one or more second ends of the optical fibers in each of the one or more rows have a similar position relative to the pars plana of the eye.

Figure 7:
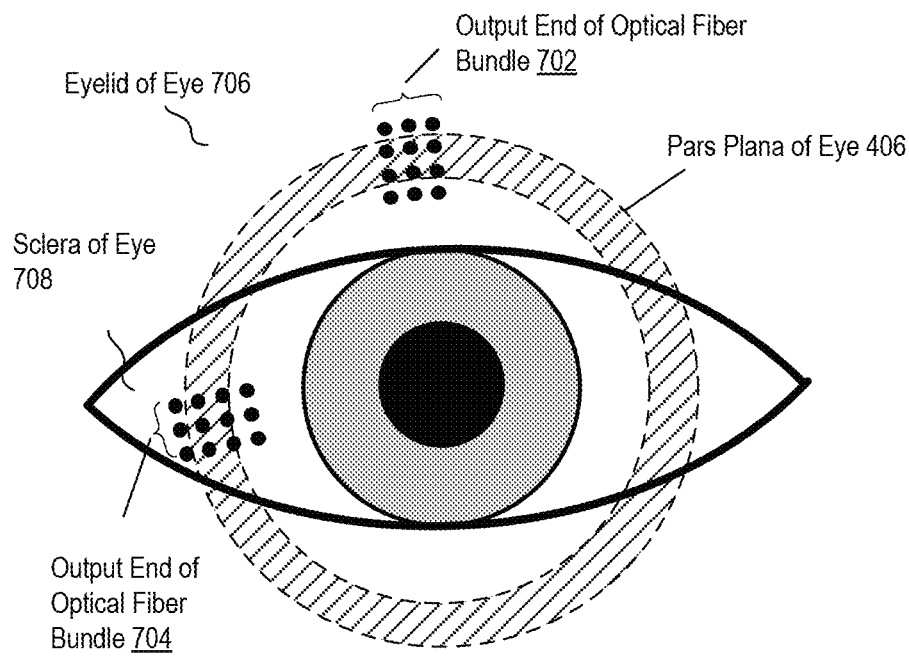
FIG. 7 shows two exemplary positions of an output end of an optical fiber bundle illuminator to perform trans-pars-planar illumination of an interior fundus of an eye.

FIG. 7 shows two exemplary positions, where an output end of the optical fiber bundle illuminator, are disposed relative to the pars plana of an eye. The output end of the optical fiber bundle illuminator 704 may be disposed directly on a sclera of the eye 708 around a pars planar area of the eye. A portion of the light from the output end of the optical fiber bundle 704 is delivered through the pars plana of the eye into the interior of the eye. Alternatively, the output end of the optical fiber bundle 702 may be disposed on an eyelid of the eye 706 around the pars plana of the eye 406. A portion of the light from the output end of the optical fiber bundle illuminator 702 is delivered through the eyelid and then through the pars plana of the eye into the interior of the eye. The position of the output end of optical fiber bundle illuminator 702 may be desirable since it avoids making direct contact with the pars plana or the sclera of the eye, thus may be less uncomfortable and safer to the eye.

Figure 8:
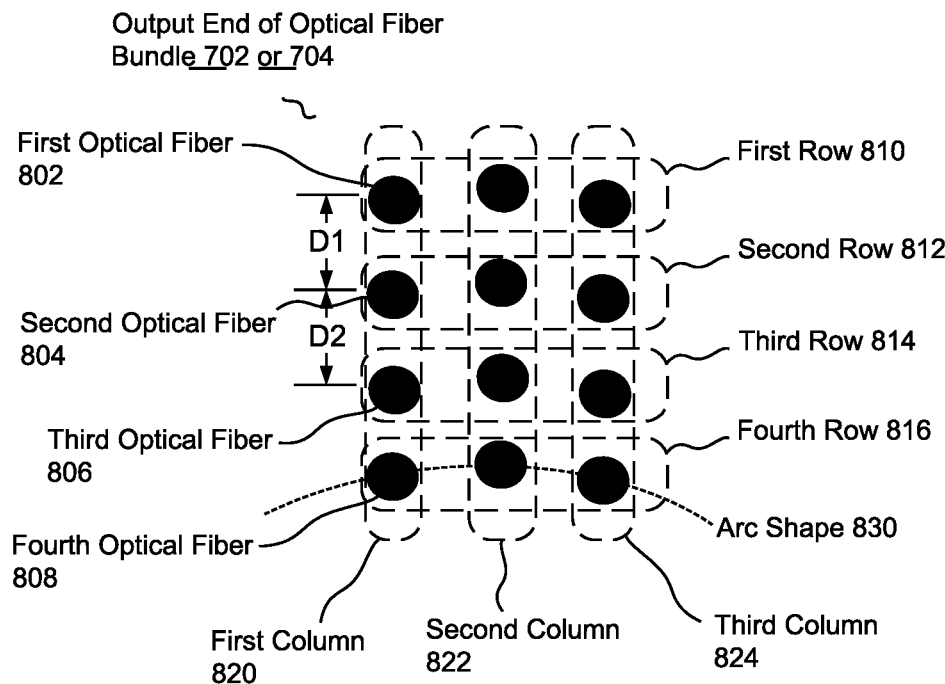
FIG. 8 shows an exemplary implementation of the output end of the optical fiber bundle illumination in FIG. 7.

FIG. 8 shows the pre-defined pattern of second ends of optical fibers of FIG. 7 in greater detail. The output end of the optical fiber bundle 702 or 704 is arranged as the pre-defined pattern comprising four rows (810, 812, 814, and 816) and three columns (820, 822, and 824), and second ends of the optical fibers in each row has an arc shape 830, whose curvature is similar to a curvature of a pars planar area of the eye. When the output end of the optical fiber bundle illuminator 702 or 704 is disposed at the positions described in FIG. 7, a first row of second ends of optical fibers 810 including a second end of a first optical fiber 802 may be disposed at a posterior of the pars plana of the eye; a second row of second ends of optical fibers 812 including a second end of a second optical fiber 804 may be disposed at the pars plana of the eye; a third row of second ends of optical fibers 814 including a second end of a third optical fiber 806 may be disposed at an anterior of the pars plana of the eye; and a fourth row of second ends of optical fibers 816 including a second end of a fourth optical fiber 808 may be disposed at the anterior of the pars plana of the eye.

Spacing between adjacent second ends of optical fibers in each row or column is a pre-defined distance. The pre-defined distance may be the same for all optical fibers or different from one optical fiber to another optical fiber. The pre-defined distance may be a fixed value or adjustable depending on a size of the pars plana of the eye. As shown in FIG. 8, the second ends of the first optical fiber and the second optical fiber may be spaced by a first pre-defined distance D1. The second ends of the second optical fiber and the third optical fiber may be displaced by a second pre-defined distance D2. The first pre-defined distance D1 and the second pre-defined distance D2 may be a fixed length, such as 1 mm, 2.5 mm, or a length between 0 and 10 mm. Alternatively, the first pre-defined distance D1 and the second pre-defined distance D2 may be determined by a size of the pars plana of the eye, such as a third of the size of the pars plana of the eye or a ratio of the size of the pars plana of the eye between 0.001 to 1. The first pre-defined distance D1 and the second pre-defined distance D2 may be same or different.

Because illumination of an interior of an eye is sensitive to a light delivery location relative to the pars plana, the disclosure provides a fast and convenient method for improving the quality of the wide-angle fundus photography by automatic localization of a pars planar area of the eye and optimization of the illumination of the interior fundus of the eye. The quality of the wide-angle fundus photography is sensitive to the illumination of the interior of the eye, and thus the quality of the wide-angle fundus photography is sensitive to the light delivery location. When light is switched sequentially between subsets of one or more optical fibers in the optical fiber bundle, the light delivery location sequentially changes relative to the pars plana of the eye, automatically improving the quality of the wide-angle fundus photography. For example, an optic disc, some choroidal structures and highly pigmented areas of the eye may be imaged with high quality when a light delivery location is at an posterior of the pars plana; retinal vascular structures of the eye may be imaged with high quality when a light delivery location is at the pars plana; and a retinal area of the eye may be imaged with poor quality when a light delivery location is at an anterior of the pars plana.

In one embodiment, the optical switching device 104 may sequentially deliver light into subsets of one or more optical fibers, the light delivery locations corresponding to the subsets of one or more optical fibers sequentially change, and the optical imager 108 sequentially forms optical images and sequentially outputs image data corresponding to the light delivered from the subsets of one or more optical fibers respectively. The controller 110 may obtain the image data from the optical imager 108, determine a ranking score for each image data according to a pre-defined ranking algorithm, and select the image data with a higher ranking score as high-ranking image data, and output the high-ranking image data. The pre-defined ranking algorithm may be a quantitative image feature analysis of the image data. The quantitative image feature analysis may include a quantitative analysis of a property of image data, and the property includes, but is not limited to, an intensity, a contrast, or a spectral property. For example, when image data has a higher contrast, the image data may be determined to have a higher ranking score.

For example, in FIG. 8, when the optical switching device 104 delivers light into the first row of optical fibers 810, the optical imager may form a first optical image and output first image data. When the optical switching device delivers light into the second row of optical fibers 812, the optical imager may form a second optical image and output second image data. When the optical switching device delivers light into the third row of optical fibers 814, the optical imager may form a third optical image and output third image data. When the optical switching device delivers light into the fourth row of optical fibers 816, the optical imager may form a fourth optical image and output fourth image data. The controller 110 may obtain the first, second, third, and fourth image data; determine a first, second, third, fourth ranking score for the first, second, and third image data respectively based on a pre-defined ranking algorithm; select high-ranking image data among the first, second, third, and fourth image data based on their ranking scores; and output the high-ranking image data.

In another embodiment, light with different colors may be delivered into one or more optical fibers at the same time to achieve desired illumination effect. For example, because a combination of red, green, and blue light can achieve similar illumination effect as white light, white light illumination of the interior of the eye may be improved by the combination of red, green and blue light. For one exemplary embodiment, red, green, and blue light may be simultaneously delivered into one optical fiber, such as the first optical fiber 802 in FIG. 8, to achieve white light illumination of the interior of the eye. For another exemplary embodiment, red, green, and blue light may be individually and simultaneously delivered into a subset of optical fibers, such as delivering red light into the first column of the first row of optical fibers in FIG. 8, delivering green light into the second column of the first row of optical fibers, and delivering blue light into the third column of the first row of optical fibers, to achieve white light illumination of the interior of the eye.

In another embodiment, a true-color fundus photography may be achieved when the optical switching device 104 sequentially deliver light with different colors into one or more optical fibers. A white light illumination may not be able to provide a true-color fundus photography since an illumination efficiency of the interior of the eye depends on a light wavelength. In the disclosed embodiment, the light with different colors delivered into the one or more optical fibers may have different light intensities to achieve spectral compensation so that a true-color fundus photography can be achieved.

In this disclosed embodiment, when the optical switching device 104 sequentially delivers light with different colors into one or more optical fibers, the optical imager 108 sequentially forms optical images and sequentially outputs image data corresponding to the light with different colors. The controller 110 may obtain the image data from the optical imager 108, overlay the image data according to a pre-defined overlay algorithm, and output the overlay image data as a true-color fundus image. In one example, red, green, and blue light may be sequentially delivered into an optical fiber, such as the first optical fiber 802 in FIG. 8, and the optical imager 108 may sequentially form a first, second, and third optical image and sequentially output first, second, and third image data. Alternatively in another example, red, green, and blue light may be individually and sequentially delivered into a subset of optical fibers. For example, when red light at a first light intensity is delivered into the first column of the first row of optical fibers in FIG. 8, the optical imager 108 may form a first optical image and output first image data. When green light at a second light intensity is delivered into the second column of the first row of optical fibers, the optical imager 108 may form a second optical image and output second image data. When blue light at a third light intensity is delivered into the third column of the first row of optical fibers, the optical imager 108 may form a third optical image and output third image data. The controller 110 may obtain the first, second, and third image data from the optical imager; overlay the first, second, and third image data based on a pre-defined overlay algorithm to generate first overlay image data; and output the first overlay image data. Subsequently, the controller 110 may generate second or third overlay image data when the red, green, blue light is sequentially delivered into the second row 812 or third row 814 of optical fibers in FIG. 8 respectively. When the controller 110 generates more than one overlay image data, the controller may further determine their ranking scores based on a pre-defined ranking algorithm, select and output high-ranking overlay image data with a high ranking score as a true-color fundus image.

The pre-defined overlay algorithm may be an algorithm of assigning image data into separate channels of an overlay image data. Alternatively, the pre-defined overlay algorithm may also be an algorithm of performing image processing on the image data and then assigning the image data into separate channels of the overlay image data. The image processing may include, but not limited to, image intensity adjustment, image contrast adjustment, or image cropping. For example, the pre-defined overlay algorithm may change the intensity of the first image data by a first ratio of 1.5 and assign the intensity-changed first image data to a first channel of the overlay image data; the pre-defined overlay algorithm may change the intensity of the second image data by a second ratio of 1.8 and assign the intensity-changed second image data to a second channel of the overlay image data; and the pre-defined overlay algorithm may also change the intensity of the third image data by a third ratio of 1.3 and assign the intensity-changed second image data to a third channel of the overlay image data. In this embodiment, the first channel of the overlay image data may be a channel corresponding to a red channel, the second channel of the overlay image data may be a channel corresponding to a green channel, and the third channel of the overlay image data may be a channel corresponding to a blue channel.

Alternatively, a true-color fundus photography may also be achieved when light with different colors is sequentially delivered into different subsets of one or more optical fibers respectively. For example, when red light at a first light intensity is delivered into the first column of optical fibers 820 in FIG. 8, the optical imager 108 may form a first optical image and output first image data. When green light at a second light is delivered into the second column of optical fibers 822, the optical imager 108 may form a second optical image and output second image data. When blue light at a third light intensity is delivered into the third column of optical fibers 824, the optical imager 108 may form a third optical image and output third image data. The controller 110 may obtain the first, second, and third image data from the optical imager 108; overlay the first, second, and third image data based on a pre-defined overlay algorithm to generate overlay image data; and output the overlay image data as a true-color fundus image.

Second ends of optical fibers in the optical fiber bundle are not limited to only an array of three columns and four rows as described in FIGS. 7 and 8. The second ends of the optical fibers may be arranged in any pattern with any number of optical fibers in different implementations. When the second ends of the optical fibers are arranged as an array, a number of columns of the array may be any integer number to provide sufficient illumination of an interior of the eye, and a number of rows of the array may be any integer number.

In another embodiment, the optical imager 108 may be an existing fundus camera so that imaging quality and view field of the existing fundus camera may be improved with the present disclosed trans-pars-planar illumination method. For example, the existing fundus camera may be an indirect ophthalmoscope. The indirect ophthalmoscope may output the optical image of the interior of the eye so that users may directly examine the optical image. Alternatively, the indirect ophthalmoscope may be equipped with a camera to record the optical image. For example, the camera may be a digital camera to transform the optical image into image data, and output or save the image data.

In another embodiment, the output end of the optical fiber bundle 106 may be packaged as an illuminator head so that the illuminator head may be used as a handheld device, wherein the term "illuminator head" is used herein to mean a terminal of the optical fiber bundle illuminator comprising one or more second end of the one or more optical fibers and configured to deliver light. When the illuminator head is disposed either directly on the sclera or on the eyelid close to a pars planar area of an eye, light from at least one optical fiber in the optical fiber bundle may be delivered through the pars plana of the eye to illuminate the interior of the eye.

In another embodiment, when a size of a light source is small, the light source may deliver light into an interior of an eye without an optical switch device or an optical fiber bundle. The light source may be in communication with a controller 101 and receive light delivering parameters from the controller. The light delivering parameters may include, but not limited to, a turn-on time, a turn-off time, a light intensity, or a light color. For example, due to a small size of a light-emitting diode (LED), one or more LEDs, such as a LED light source array, may be placed either on a sclera or an eyelid of the eye, delivering light through a pars planar area of the eye into the fundus of the eye 404 for illumination.

In another embodiment, the output end of the optical fiber bundle 106 may be packaged as an illuminator head so that the illuminator head may be mounted to a chinrest or helmet based wearable device. A connection between the illuminator head to the chinrest or helmet based wearable device is adapted to hold the illuminator head steady and also is adjustable so that users may adjust a position or an orientation of the illuminator head freely. For example, the connection may be a foldable arm comprising at least two segments or an adjustable gooseneck. The disclosed embodiment may free the user's hand for holding the illuminator head, reduce light fluctuation and improve the quality of the fundus photography due to an increased stability of the illuminator head.

Figure 9A:
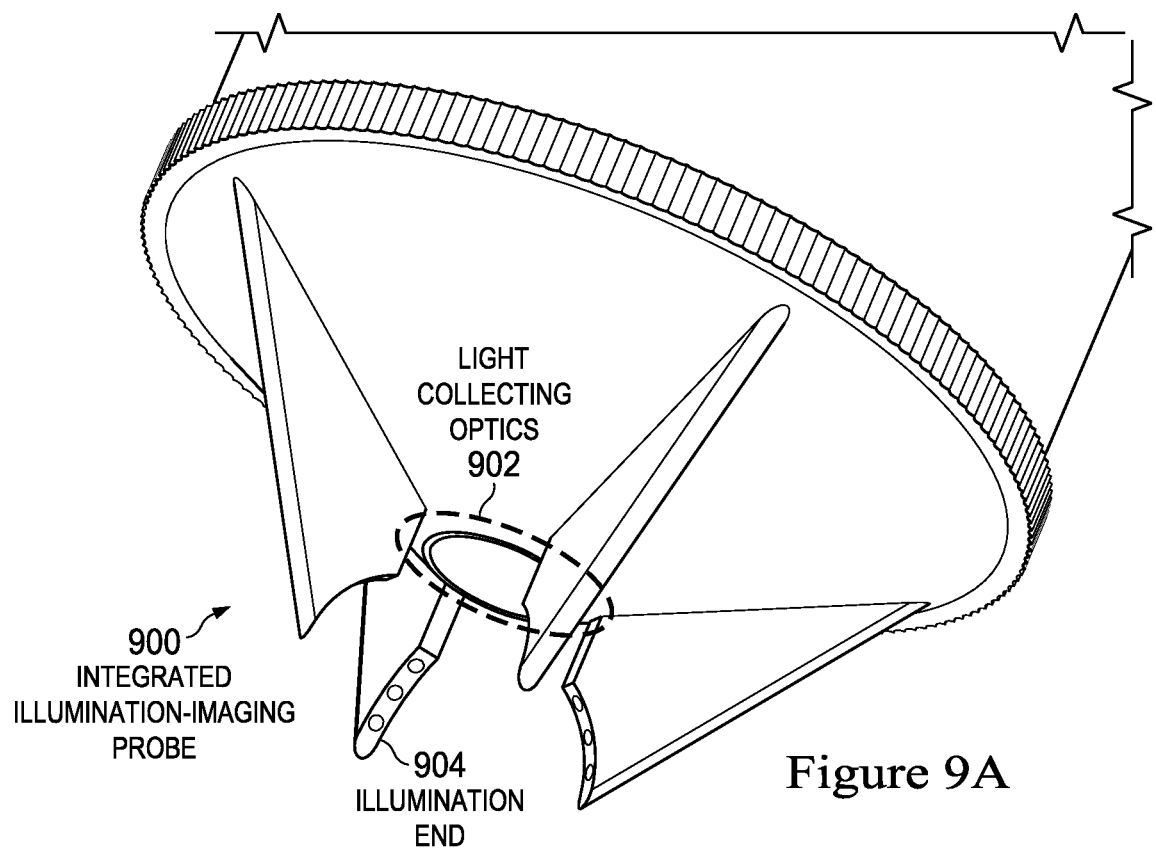
FIG. 9A shows an exemplary implementation of an integrated illumination-imaging probe for performing fundus imaging with trans-pars-planar illumination.

In another embodiment, the output end of the optical fiber bundle illuminator 106 may be integrated with a light collecting optics in the optical imager as a device for easy illumination and imaging of the interior of the eye. FIG. 9A shows an exemplary embodiment of an integrated illumination-imaging probe 900 by integrating the output end of the optical fiber bundle 106 and the light collecting optics in the optical imager 108. In FIG. 9A, an illumination end 904 comprises a portion of the second ends of optical fiber bundle and delivery light into the eye. The embodiment in FIG. 9A comprises four illumination ends surrounding the light collecting optics 902 at the center. The illumination end 904 may have a curvature similar to the curvature of a sclera of the eye. When the integrated illumination-imaging probe 900 is disposed close to the eye, the four illumination ends may be configured be adjacent to a sclera 708 or an eyelid 706 of the eye and the light collecting optics 902 in the middle may be configured adjacent to cornea of the eye. A portion of the light from the four illumination ends is delivered through the pars plana of the eye to illuminate the interior of the eye, and the light collecting optics 902 collects imaging light through pupil from the interior of the eye. A number of illumination ends in the integrated illumination-imaging probe is not limited to four as shown in FIG. 9A. For example, the number of illumination ends in the integrated illumination-imaging probe may be one, two or any integer number larger than two.

Figure 9B:
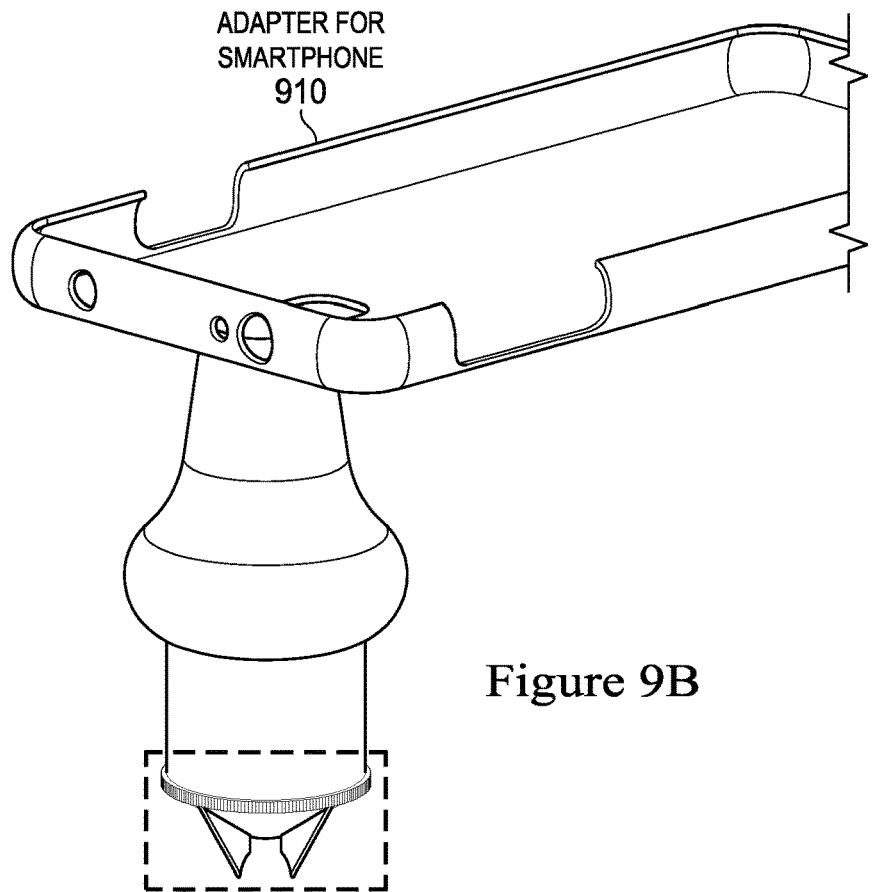
FIG. 9B shows an exemplary implementation of an integrated illumination-imaging probe with an adapter for using with a smartphone.

In one embodiment, an integrated illumination-imaging probe 900 may be configured to be used with a handheld electronic device with a camera, such as a smartphone. For example, in FIG. 9B, the integrated illumination-imaging probe 900 is integrated with a light source 102, a light switching device 104, imaging optics in an optical imager, and an adapter 910 configured to be connected with a smartphone. In this embodiment, the integrated illumination-imaging probe 900 delivers light through a pars planar area of the eye for illumination and collects light through a pupil of the eye from the interior of the eye. The adapter for a smartphone 910 is configured to use a camera lens of the camera of the smartphone to form an optical image from the light collected by the light collecting optics 902. A camera sensor of the camera may transform the optical image into image data and output the image data. The image data may be further displayed on a display of the smartphone for clinical examination. Alternatively, the image data may be further transmitted by the smartphone to a network for telemedicine.

Figure 9C:
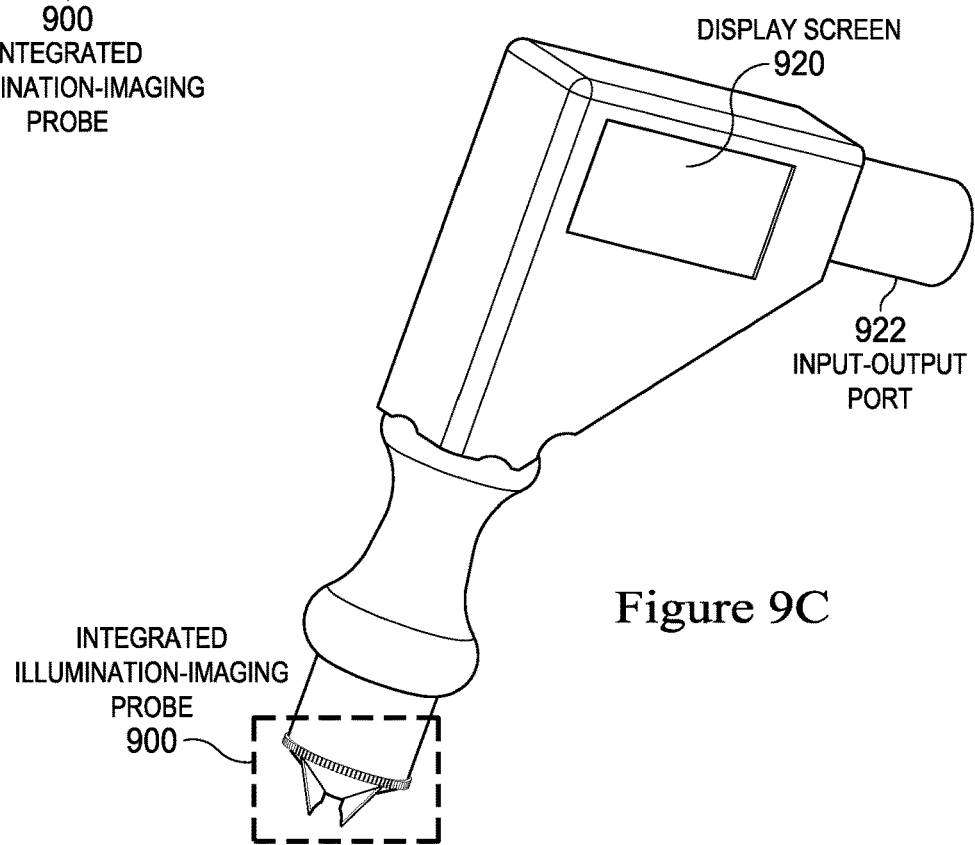
FIG. 9C shows an exemplary implementation of an integrated illumination-imaging probe being integrated to be a stand-alone handheld device for performing fundus imaging with trans-pars-planar illumination.

In another embodiment, the integrated illumination-imaging probe may be integrated further with other devices to build a stand-alone fundus camera. For example, as shown in FIG. 9C, the integrated illumination-imaging probe 900 is integrated with a light source 102, a light switch device 104, an optical fiber bundle illuminator 106, an optical imager 108, and a controller 110 to build the stand-alone fundus camera. The stand-alone fundus camera may include a display screen 920 to display image data. The stand-alone fundus camera may include an input-output port 922 to communicate with other device or a network.

Figure 10:
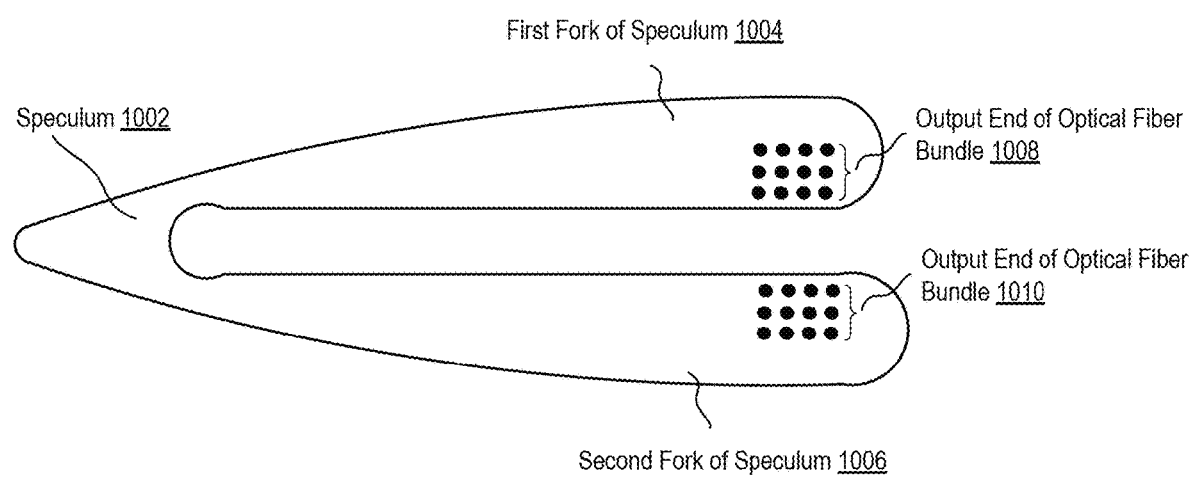
FIG. 10 shows an exemplary implementation of attaching an output end of an optical fiber bundle illuminator to a fork of an eye speculum for illuminating the fundus of an eye.

In another embodiment, the output end of the optical fiber bundle illuminator may be integrated with one or more forks of an eye speculum to illuminate the fundus of an eye. The output end of the optical fiber bundle illuminator may be attached to the one or more forks of the eye speculum at locations where the one or more forks of the eye speculum touch a sclera or an eyelid of the eye, so that light from the output end of the optical fiber bundle illuminator may be delivered through the pars plana of the eye into the interior of the eye for illumination. The output end of the optical fiber bundle illuminator may be attached to the one or more forks of the eye speculum with several configurations, such as at the inner surface of the one or more forks, at the outer surface of the one or more forks, or inside the body of the one or more forks of the speculum. The speculum may be either a reusable eye speculum or a disposable eye speculum. FIG. 10 shows an exemplary embodiment of a pattern of an output end of an optical fiber bundle at two forks of a eye speculum 1002. The output end of the optical fiber bundle 1008 is attached to a first fork of the eye speculum 1004, and the output end of optical fiber bundle illuminator 1010 is attached to a second fork of the eye speculum 1006. FIG. 10 shows the output end of optical fiber bundle illuminator 1008 and 1010 are arranged in the same pattern. Alternatively, the output end of optical fiber bundle 1008 and 1010 may be arranged in different patterns.

In another embodiment, when an optical fiber bundle illuminator 106 deliver illuminating light through a pars planar area into an interior of an eye and an optical imager 108 may collect imaging light through a pupil from the fundus of the eye, the imaging light may comprise light having different wavelength as the illuminating light. For example, the imaging light may comprise longer wavelength light, such as, fluorescent light, than the illuminating light. In this embodiment, the present disclosure may be used for fluorescence angiography.

Figure 11:
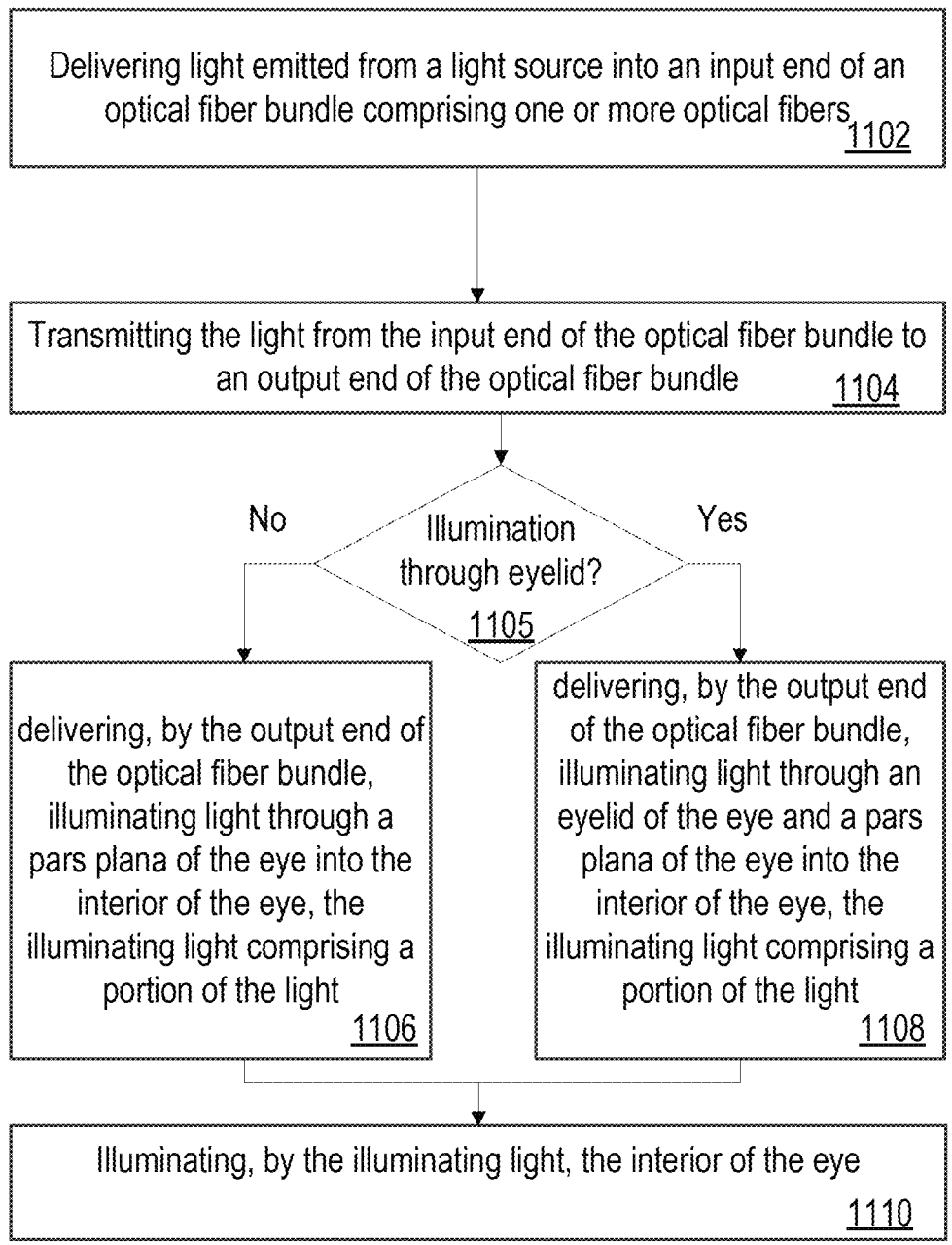
FIG. 11 shows a block diagram of a method of trans-pars-planar illumination of the fundus of an eye.

FIG. 11 shows an embodiment of the method of illuminating an interior of an eye 404 utilizing the system described above. In step 1102, light emitted from a light source 102 is delivered into an input end of an optical fiber bundle comprising one or more optical fibers. In step 1104, the light from the input end of the optical fiber bundle 106 is transmitted to an output end of the optical fiber bundle. In step 1105, whether illumination is through an eyelid of the eye is determined. When a result of the determination is no, in step 1106, the output end of the optical fiber bundle delivers illuminating light through a pars plana of the eye into the interior of the eye. Alternatively, when a result of the determination is yes, in step 1108, the output end of the optical fiber bundle delivers illuminating light through the eyelid of the eye and the pars plana of the eye into the interior of the eye. The illuminating light may comprises a portion of the light. In step 1110, the portion of the light entering into the interior of the eye illuminates the interior of the eye.

The light source 102 may include one or more light sources, and each light source may be one of a visible light source, a near infrared light source, an infrared light source, and an ultra-violet light source. When the light source is a visible light source, the light source may be one of a white light source or a color light source. When the light source is a color light source, the light source 102 may be configured to emit one color or a combination of multiple colors.

Figure 12:
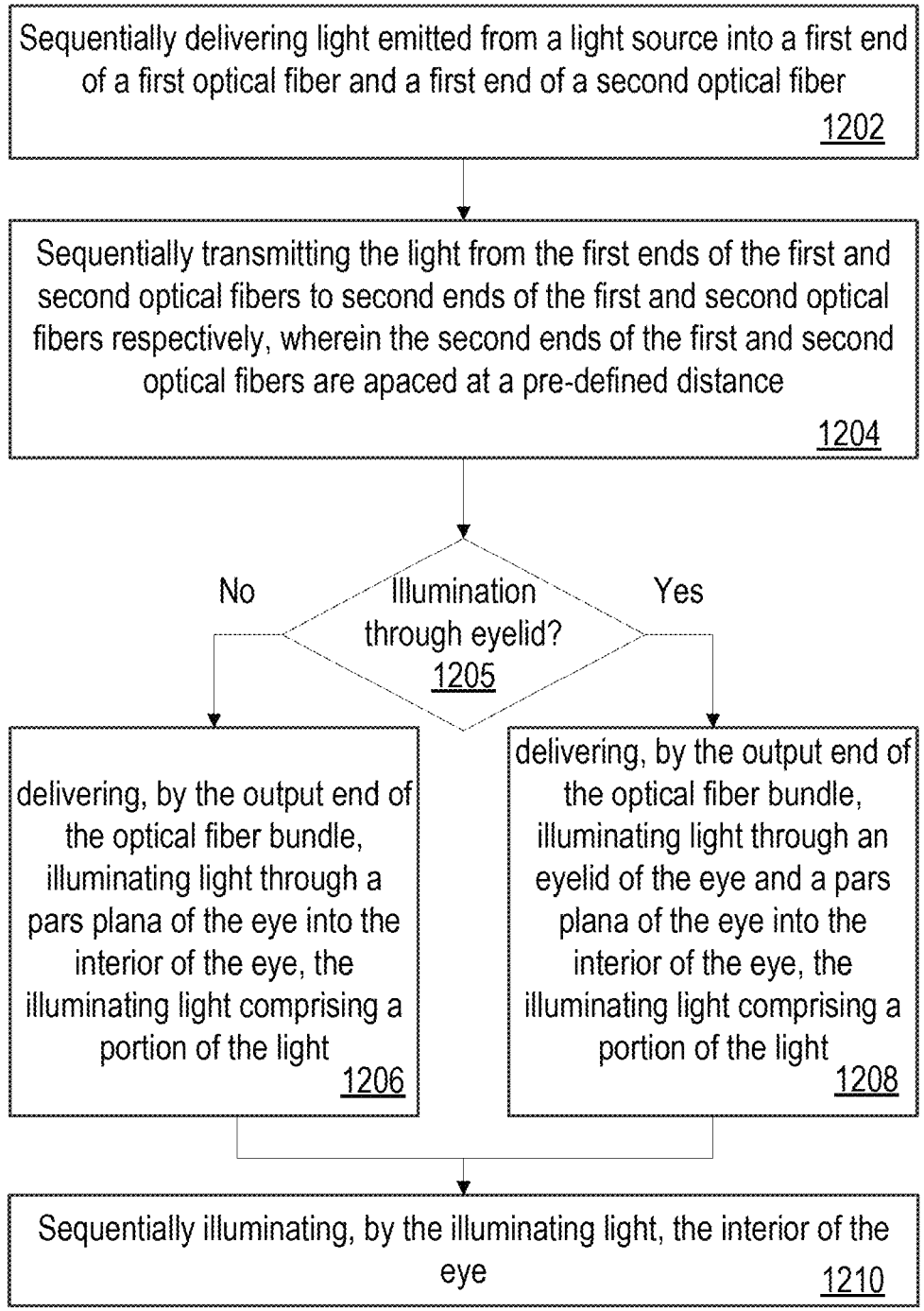
FIG. 12 shows a block diagram of a method of sequentially illuminating the fundus of an eye by individual illumination channels of the fiber bundle illuminator in FIGS. 7-10.

FIG. 12 shows another embodiment of the method of illuminating the interior of the eye 404 utilizing the system described above. In step 1202, the light emitted from the light source 102 may be sequentially delivered into the first end of the first optical fiber and the first end of the second optical fiber. In step 1204, the light from the first ends of the first and second optical fibers is sequentially transmitted to the second ends of the first and second optical fibers respectively, wherein the second ends of the first and second optical fibers are spaced at a pre-defined distance. In step 1205, whether illumination is through an eyelid of the eye is determined. When a result of the determination is no, in step 1206, the second ends of the first and second optical fibers sequentially deliver illuminating light through the pars plana of the eye into the interior of the eye. Alternatively, when a result of the determination is yes, in step 1208, the second ends of the first and second optical fibers sequentially deliver illuminating light through the eyelid of the eye and the pars plana of the eye into the interior of the eye. The illuminating light may include a portion of the light. In step 1210, the illuminating light entering into the interior of the eye sequentially illuminates the interior of the eye. In this method, while maintaining the output end of the optical fiber bundle stationary relative to the pars plana of the eye, light delivery locations corresponding to the first and second optical fibers sequentially change. Because the illumination of the interior of the eye depends on the light delivery locations, the quality of the illumination of the interior of the eye changes sequentially so that an optimized illumination of the interior of the eye may be achieved.

Figure 13:
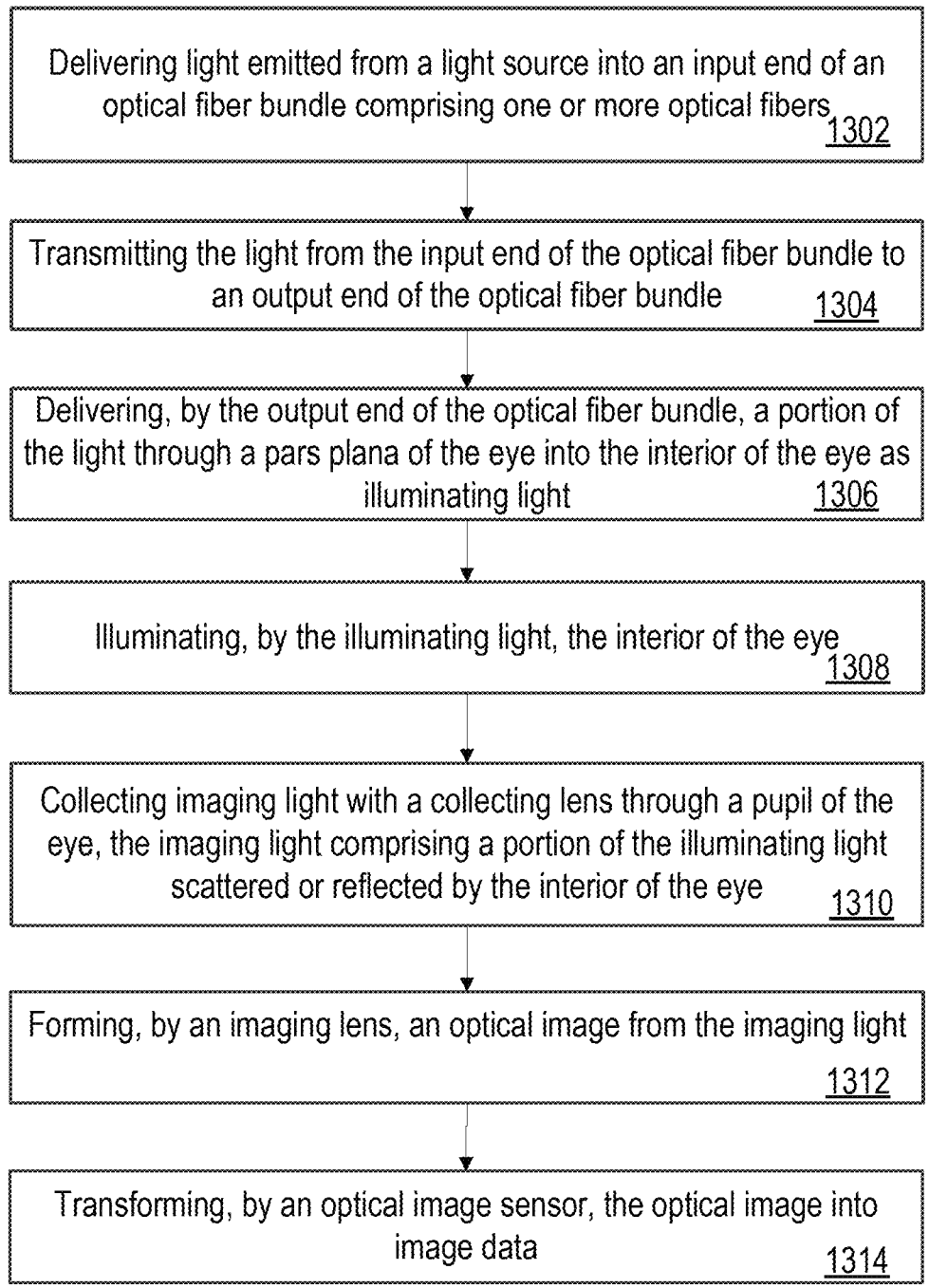
FIG. 13 shows a block diagram of a method of preforming wide-angle fundus photography with trans-pars-planar illumination.

FIG. 13 shows one embodiment of the method of performing fundus photography of an eye 402 utilizing the system described above. In step 1302, light emitted from a light source 102 is delivered into an input end of an optical fiber bundle illuminator 106 comprising one or more optical fibers. In step 1304, the light from the input end of the optical fiber bundle is transmitted to an output end of the optical fiber bundle. In step 1306, the output end of the optical fiber bundle delivers a portion of the light through the pars plana of the eye into the interior of the eye as illuminating light. In step 1308, the illuminating light illuminates the interior of the eye 404. In step 1310, imaging light is collected with a collecting lens 502 through a pupil of the eye, wherein the imaging light comprises a portion of the illuminating light scattered or reflected by the interior of the eye 404. In step 1312, an imaging lens 504 forms an optical image from the imaging light. In step 1314, an optical image sensor 506 transforms the optical image into image data.

FIG. 14A shows an alternative step 1402 that may be substituted for step 1302. In step 1402, the light emitted from a light source 102 is delivered into an input end of an optical fiber bundle 106 comprising a first optical fiber and a second optical fiber, wherein the light comprises a first light and a second light. FIG. 14B shows an alternative step 1404 that may be substituted for step 1304. In step 1404, a light switch device 104 sequentially delivers the first light into the first end of the first optical fiber and second light into the first end of the second optical fiber. FIG. 14C shows an alternative step 1406 that may be substituted for step 1314. In step 1406, the imaging lens 504 forms a first optical image from the imaging light when the imaging light is from the first light from the first optical fiber, and the imaging lens forms a second optical image from the imaging light when the imaging light is from the second light from the second optical fiber.

Figure 15:
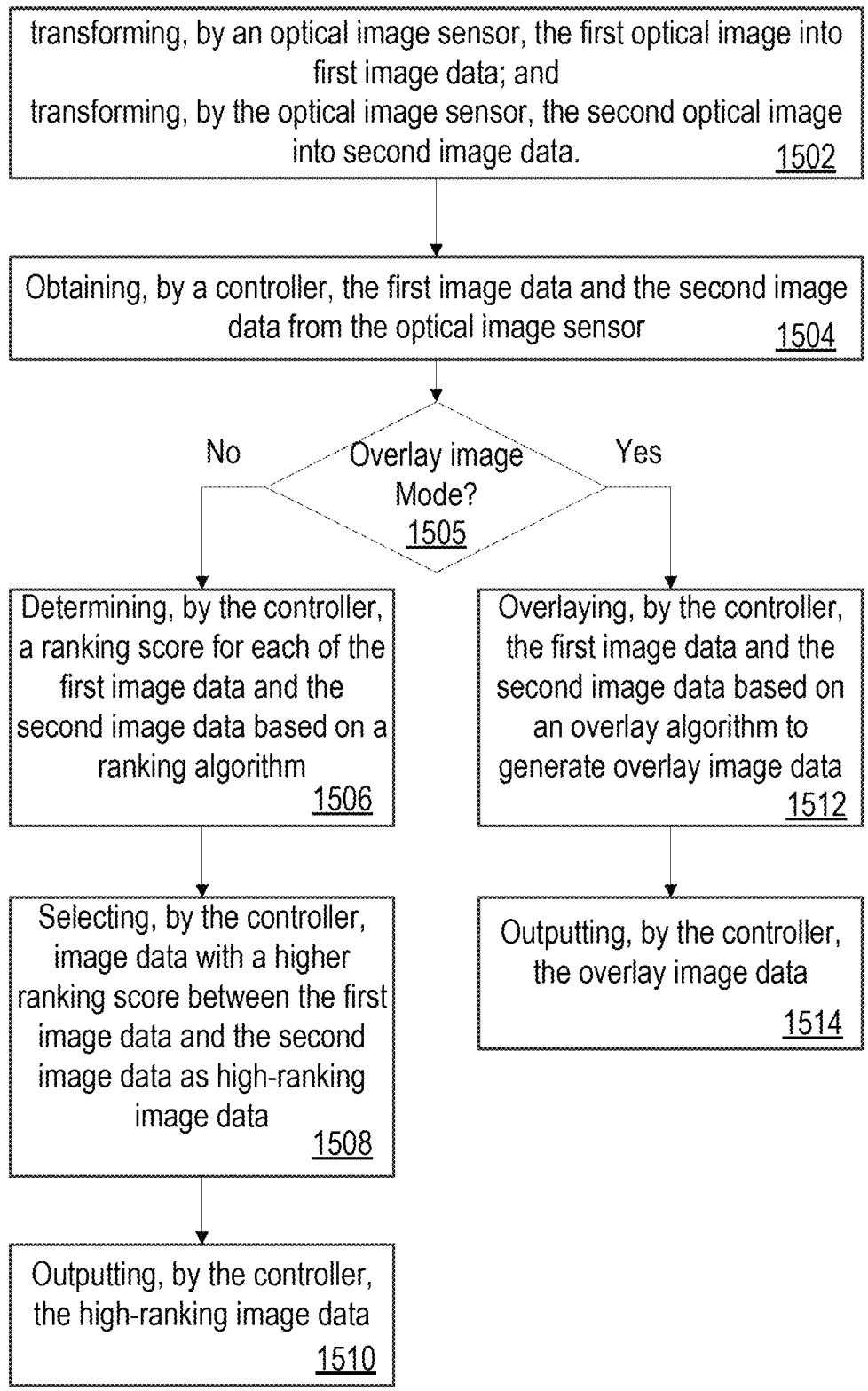
FIG. 15 shows a block diagram of a method of outputting high-ranking image data or overlay image data.

FIG. 15 shows one embodiment of the method of selecting high quality image data when the light is sequentially delivered into the first and second optical fibers. In step 1502, an optical image sensor 506 transform the first optical image into first image data, and transforms the second optical image into second image data. In step 1504, a controller 110 obtains the first image data and the second image data from the optical image sensor 506. In step 1505, whether an overlay image mode is selected is determined. When a result of the determination is no, in step 1506, the controller 110 determines a ranking score for each of the first image data and the second image data based on a ranking algorithm. In step 1508, the controller 110 selects image data with a higher ranking score between the first image data and second image data as high-ranking image data. In step 15010, the controller 110 output the high-ranking image data.

The pre-defined ranking algorithm may be a quantitative image feature analysis of the image data. The quantitative image feature analysis may include a quantitative analysis of a property of image data, and the property includes, but is not limited to, an intensity, a contrast, or a spectral property. For example, when image data has a higher contrast, the image data may be determined to have a higher ranking score.

Alternatively, when a result of the determination in step 1505 is no, FIG. 15 shows another embodiment of the method of generating overlay image data. In this embodiment, in step 1512, the controller 110 overlays the first image data and the second image data based on an overlay algorithm to generate overlay image data, and in step 1514, the controller 110 outputs the overlay image data.

The overlay algorithm may be an algorithm of assigning the image data into separate channels of the overlay image data. Alternatively, the overlay algorithm may also be an algorithm of performing image processing on the image data and then assigning the image data into separate channels of the overlay image data. The image processing may include, but not limited to, image intensity adjustment, image contrast adjustment, or image cropping. For example, the overlay algorithm may change the intensity of the first image data by a first ratio of 1.5 and assign the intensity-changed first image data to a first channel of the overlay image data; and the overlay algorithm may also change the intensity of the second image data by a second ratio of 1.8 and assign the intensity-changed second image data to a second channel of the overlay image data. In this embodiment, the first channel of the overlay image data may be a channel corresponding to a red channel, and the second channel of the overlay image data may be a channel corresponding to a green channel.

In all disclosed embodiments, the light may be white light or color light, the optical fiber bundle illuminator may comprise one or more optical fibers, and there may be one or more lights delivered into subsets of the one or more optical fibers sequentially or simultaneously. For example, red, green and blue lights with different light intensities may be delivered into a first, second, and third optical fiber sequentially, and the controller outputs overlay image data so that a true-color fundus photography is achieved to compensate for the efficiency difference of light colors through the pars plana.

While the particular disclosure has been described with reference to illustrative embodiments, this description is not meant to be limiting. Various modifications of the illustrative embodiments and additional embodiments of the disclosure, will be apparent to one of ordinary skill in the art from this description. Those skilled in the art will readily recognize that these and various other modifications can be made to the exemplary embodiments, illustrated and described herein, without departing from the spirit and scope of the present disclosure. It is therefore contemplated that the appended claims will cover any such modifications and alternate embodiments. Certain proportions within the illustrations may be exaggerated, while other proportions may be minimized. Accordingly, the disclosure and the figures are to be regarded as illustrative rather than restrictive.

What is claimed is:

1. An apparatus for performing fundus imaging, the apparatus comprising:
    a trans-pars-planar illuminator comprising a light source and a multiple-channel light delivery element, for delivering light into a fundus of an eye through a pars plana and an adjacent area of the eye;
    an optical imaging system comprising optical elements and an optical image sensor, for collecting scattered and reflected light from the fundus illuminated by the trans-pars-planar illuminator and forming an image of the fundus through a pupil of the eye;
    a control unit comprising a light switch device and a digital processor, for controlling the trans-pars-planar illuminator and the optical imaging system, and for processing fundus images to optimize trans-pars-planar illumination and image formation; and
    a capability of sequential scanning of multiple illumination channels to optimize fundus imaging, wherein the control unit is configured to perform:
        delivering, by the light switch device in the control unit, illumination light emitted from the light source into a first channel of the trans-pars-planar illuminator,
        obtaining, from optical image sensor in the optical imaging system, first image data corresponding the first channel illumination, wherein the illumination light enters a first location relative to the pars plana,
        delivering, by the light switch device in the control unit, the illumination light emitted from the light source into a second channel of the trans-pars-planar illuminator,
        obtaining, from optical image sensor in the optical imaging system, second image data corresponding the second channel illumination, wherein the illumination light enters a second location relative to the pars plana,
        determining, by the processor in the control unit, a ranking score for each of the first image data and the second image data based on a ranking algorithm,
        selecting, by the processor in the control unit, image data with a higher ranking score between the first image data and the second image data as a high-ranking image data, and
        outputting, by the processor in the control unit, the high-ranking image data corresponding to an illumination location through the pars plana.

2. The apparatus according to claim 1, wherein the trans-pars-planar illuminator comprises:
    a light source;
    an optical fiber bundle as the multiple-channel light delivery element capable of performing:
        delivering illumination light emitted from a light source into an input end of the optical fiber bundle comprising at least a first optical fiber and a second optical fiber;
        transmitting, by the optical fiber bundle, the light from the input end of the optical fiber bundle to an output end of the optical fiber bundle;
        delivering, for the output end of the optical fiber bundle, illuminating light to the fundus of the eye through the pars plana and the adjacent area of the eye.

3. The apparatus according to claim 2, wherein the light source comprises at least one of:
    a white light source;
    a color light source configured to emit one or more colors;
    a near infrared light source; or
    an infrared light source.

4. The apparatus according to claim 1, wherein the trans-pars-planar illuminator comprises:
    a light source array with a predefined distance as the multiple-channel light delivery element to delivery illuminating light to the fundus of the eye through the pars planar and the adjacent area.

5. The apparatus according to claim 1, wherein the trans-pars-planar illuminator is configured to be contacted with a sclera of the eye to delivery light into the fundus of the eye through the pars plana and an adjacent scleral area of the eye.

6. The apparatus according to claim 1, wherein the trans-pars-planar illuminator is configured to be contacted with an eyelid of the eye to delivery light into the fundus of the eye through the eyelid and a sclera of the eye.

7. The apparatus according to claim 1, wherein the trans-pars-planar illuminator is configured to be a separate illumination device.

8. The apparatus according to claim 1, wherein the trans-pars-planar illuminator is configured to be attached to a fork of an eye speculum.

9. The apparatus according to claim 1, wherein the trans-pars-planar illuminator is configured to be integrated to a fundus imaging system.

10. The apparatus according to claim 1, wherein the trans-pars-planar illuminator is configured to adapt to existing fundus imaging system.

11. The apparatus according to claim 1, wherein the apparatus is configured to be a portable fundus camera.

12. The apparatus according to claim 1, wherein the apparatus is configured to be a stand-alone fundus camera.

13. The apparatus according to claim 1, wherein the apparatus is configured to be a non-mydriatic imaging device.

14. The apparatus according to claim 1, wherein the apparatus is configured to be a mydriatic imaging device.

15. An apparatus for performing fundus imaging, the apparatus comprising:
- a trans-pars-planar illuminator comprising a light source and a multiple-channel light delivery element, for delivering light into a fundus of an eye through a pars plana and an adjacent area of the eye;
- an optical imaging system comprising optical elements and an optical image sensor, for collecting scattered and reflected light from the fundus illuminated by the trans-pars-planar illuminator and forming an image of the fundus through a pupil of the eye;
- a control unit comprising a light switch device and a digital processor, for controlling the trans-pars-planar illuminator and the optical imaging system, and for processing fundus images to optimize trans-pars-planar illumination and image formation; and
- a capability of true color imaging, wherein:
  - illumination light emitted from a light source in the trans-pars-planar illuminator comprises at least a first light color and a second light color; and
  - the control unit is configured to perform:
    - delivering, by the light switch device in the trans-pars-planar illuminator, the first light color with predefined light intensity, into the fundus of an eye;
    - obtaining, from optical image sensor in the optical imaging system, first image data corresponding the first color illumination;
    - delivering, by the light switch device in the trans-pars-planar illuminator, the second light color with predefined light intensity, into the fundus of an eye;
    - obtaining, from optical image sensor in the optical imaging system, second image data corresponding the second color illumination;
    - overlaying, by the processor in the control unit, the first image data and the second image data based on an overlay algorithm to generate a true color image to balance efficiency difference of different light colors; and
    - outputting, by the processor in the control unit, the true color image.

16. An apparatus for performing fundus imaging, the apparatus comprising:
- a trans-pars-planar illuminator comprising a light source and a multiple-channel light delivery element, for delivering light into a fundus of an eye through a pars plana and an adjacent area of the eye;
- an optical imaging system comprising optical elements and an optical image sensor, for collecting scattered and reflected light from the fundus illuminated by the trans-pars-planar illuminator and forming an image of the fundus through a pupil of the eye;
- a control unit comprising a light switch device and a digital processor, for controlling the trans-pars-planar illuminator and the optical imaging system, and for processing fundus images to optimize trans-pars-planar illumination and image formation; and
- a capability of selective imaging of choroidal and retinal structures, wherein:
  - illumination light emitted from a light source in the trans-pars-planar illuminator comprises at least a first light and a second light, wherein the first light is a near infrared light and the second light is a visible light; and
  - the control unit is configured to perform:
    - delivering, by the light switch device in the trans-pars-planar illuminator, the near infrared light, into the fundus of an eye;
    - obtaining, from optical image sensor in the optical imaging system, first image data of choroidal structure corresponding first near infrared illumination;
    - delivering, by the light switch device in the trans-pars-planar illuminator, the visible light, into the fundus of the eye; and
    - obtaining, from optical image sensor in the optical imaging system, second image data of retinal structure corresponding second visible light illumination.

17. An apparatus for performing fundus imaging, the apparatus comprising:
- a trans-pars-planar illuminator comprising a light source and a multiple-channel light delivery element, for delivering light into a fundus of an eye through a pars plana and an adjacent area of the eye;
- an optical imaging system comprising optical elements and an optical image sensor, for collecting scattered and reflected light from the fundus illuminated by the trans-pars-planar illuminator and forming an image of the fundus through a pupil of the eye;
- a control unit comprising a light switch device and a digital processor, for controlling the trans-pars-planar illuminator and the optical imaging system, and for processing fundus images to optimize trans-pars-planar illumination and image formation; and
- a capability of pars-planar-identification and illumination guidance, wherein:
  - illumination light comprises at least a first light color and a second light color; and
  - the control unit is configured to perform:
    - delivering, by the light switch device in the trans-pars-planar illuminator, the first light color into each channel of the multiple-channel light delivery element of the trans-pars-planar illuminator sequentially;
    - obtaining, from optical image sensor in the optical imaging system, fundus images corresponding to each channel illumination of the multiple-channel light delivery element of the trans-pars-planar illuminator sequentially;
    - determining, by the processor in the control unit, a ranking score for each of the fundus images based on a ranking algorithm to identify a high ranking image which corresponding to an illumination location through the pars plana;
    - registering, by the processor in the control unit, an illumination location of the pars plana;
    - delivering, by the light switch device in the trans-pars-planar illuminator, the second light color to the illumination location of the pars plana; and
    - obtaining, from optical image sensor in the optical imaging system, fundus images with second light color illumination through the pars plana.

* * * * *